(12) United States Patent
Nishimaki et al.

(10) Patent No.: US 10,905,788 B2
(45) Date of Patent: Feb. 2, 2021

(54) SCENT-EMANATING APPARATUS

(71) Applicant: SONY INTERACTIVE ENTERTAINMENT INC., Tokyo (JP)

(72) Inventors: Yoichi Nishimaki, Kanagawa (JP); Shinichi Hirata, Kanagawa (JP); Yuichi Machida, Kanagawa (JP); Kazuo Miura, Kanagawa (JP)

(73) Assignee: SONY INTERACTIVE ENTERTAINMENT INC., Tokyo (JP)

( * ) Notice: Subject to any disclaimer, the term of this patent is extended or adjusted under 35 U.S.C. 154(b) by 89 days.

(21) Appl. No.: 15/773,750

(22) PCT Filed: Jul. 29, 2016

(86) PCT No.: PCT/JP2016/072309
§ 371 (c)(1),
(2) Date: May 4, 2018

(87) PCT Pub. No.: WO2017/098748
PCT Pub. Date: Jun. 15, 2017

(65) Prior Publication Data
US 2018/0318461 A1 Nov. 8, 2018

(30) Foreign Application Priority Data
Dec. 9, 2015 (JP) ................. 2015-240119

(51) Int. Cl.
*A61L 9/12* (2006.01)
*A63F 13/28* (2014.01)
(52) U.S. Cl.
CPC ................ *A61L 9/12* (2013.01); *A61L 9/122* (2013.01); *A63F 13/28* (2014.09);
(Continued)

(58) Field of Classification Search
CPC . A61L 9/03; A61L 9/032; A61L 9/035; A61L 9/037; A61L 9/04; A61L 9/042;
(Continued)

(56) References Cited

U.S. PATENT DOCUMENTS 5,571,401 A * 11/1996 Lewis .................. G01N 27/126
205/787
8,855,827 B2 * 10/2014 Weening .................. A61L 9/14
239/11
(Continued)

FOREIGN PATENT DOCUMENTS

| JP | 2003-254927 A | 9/2003 |
| JP | 2004-305302 A | 11/2004 |

(Continued)

OTHER PUBLICATIONS

International Search Report and Written Opinion dated Sep. 6, 2016, from the corresponding International Application No. PCT/JP2016/072309, 8 sheets.

(Continued)

*Primary Examiner* — Timothy C Cleveland
(74) *Attorney, Agent, or Firm* — Katten Muchin Rosenman LLP

(57) ABSTRACT

Disclosed herein is a scent-emanating apparatus including a discharging mechanism which permits a scent substance perceivable by a user together with a marker substance for detection to be discharged outwards, and a sensor to detect the marker substance discharged from the discharging mechanism.

3 Claims, 11 Drawing Sheets

(52) U.S. Cl.
CPC .... *A61L 2209/111* (2013.01); *A61L 2209/133* (2013.01); *A61L 2209/14* (2013.01); *A63F 2300/302* (2013.01)

(58) Field of Classification Search
CPC . A61L 9/044; A61L 9/046; A61L 9/12; A61L 9/122; A61L 9/125; A61L 9/127; A61L 9/14
See application file for complete search history.

(56) References Cited

U.S. PATENT DOCUMENTS

2005/0130747 A1* 6/2005 Kubby ................ A01M 1/2077
463/48
2015/0297776 A1* 10/2015 Conroy ................ G08B 23/00
239/11

FOREIGN PATENT DOCUMENTS

| JP | 2006-504491 | A | 2/2006 |
|---|---|---|---|
| JP | 2009-106402 | A | 5/2009 |
| JP | 2010-130471 | A | 6/2010 |
| JP | 2015-136631 | A | 7/2015 |
| WO | 2004/041328 | A2 | 5/2004 |

OTHER PUBLICATIONS

International Preliminary Report on Patentability dated Jun. 12, 2018, from the corresponding International Application No. PCT/JP2016/072309, 11 sheets.

Notice of Reasons for Refusal dated Jun. 9, 2020, in Japanese Patent Application No. 2018-187353, 3 sheets.

* cited by examiner

TO INFORMATION PROCESSING APPARATUS 30

US 10,905,788 B2

SCENT-EMANATING APPARATUS

TECHNICAL FIELD

The present invention relates to a scent-emanating apparatus to emanate a scent for a user, an information processing apparatus to control the scent-emanating apparatus, and a method and program for controlling the scent-emanating apparatus.

BACKGROUND ART

There has been a desire for a user of video game, for instance, to feel as if he or she were there. To attain such a desire, efforts have been made to develop a scent-emanating apparatus to emanate a specific scent for the user. This scent-emanating apparatus is so designed as to discharge a scent substance into the air so that the user smells the scent.

SUMMARY

Technical Problem

The scent-emanating apparatus mentioned above should preferably be able to prove that it has actually discharged the scent substance when emanating the scent. Unfortunately, there is an instance in which it is difficult to directly prove that the scent substance has been discharged because of the type or the like of the scent substance.

The present invention has been completed in view of the foregoing. It is an object of the present invention to provide a scent-emanating apparatus which is able to prove that a scent substance has been discharged, an information processing apparatus which controls the scent-emanating apparatus, a method for controlling the scent-emanating apparatus, and a control program.

Solution to Problem

A scent-emanating apparatus according to the present invention is one designed to emanate a scent for a user. It includes a discharging mechanism to discharge outward therefrom the scent substance, together with a marking substance for detection, and a sensor to detect the marking substance discharged by the discharging mechanism.

An information processing apparatus according to the present invention is one which is connected to a scent-emanating apparatus which includes a discharging mechanism to discharge a scent substance for a user to perceive the scent outwards from the scent-emanating apparatus, together with a marking substance for detection, and a sensor which detects the marking substance discharged from the discharging mechanism. The information processing apparatus includes an acquisition unit to acquire from the sensor the information about the result of detection of the marking substance, and a processing unit to perform the process relating to the scent-emanating apparatus in response to the acquired information about the result of detection.

A method for controlling the scent-emanating apparatus according to the present invention is intended to control the scent-emanating apparatus including the discharging mechanism to discharge a scent substance for a user to perceive the scent outwards from the scent-emanating apparatus, together with a marking substance for detection, and a sensor to detect the marking substance discharged from the discharging mechanism. The method includes a step of acquiring from the sensor the information about the result of the detection of the marking substance, and a step of performing the process relating to the scent-emanating apparatus in response to the acquired information about the result of detection.

A program pertaining to the present invention is intended to control the computer connected to the scent-emanating apparatus which includes a discharging mechanism to discharge a scent substance for a user to perceive the scent outwards from the scent-emanating apparatus, together with a marking substance for detection, and a sensor to detect the marking substance discharged from the discharging mechanism. The computer functions as an acquisition unit that acquires from the sensor the information about the result of detection of the marking substance and a processing unit that performs the process relating to the scent-emanating apparatus in response to the acquired information about the result of detection. The program may be available in the form stored in permanent memory readable by the computer.

DESCRIPTION OF EMBODIMENTS

The following is a detailed description of the embodiments of the present invention which are based on the accompanying drawings.

Figure 1:
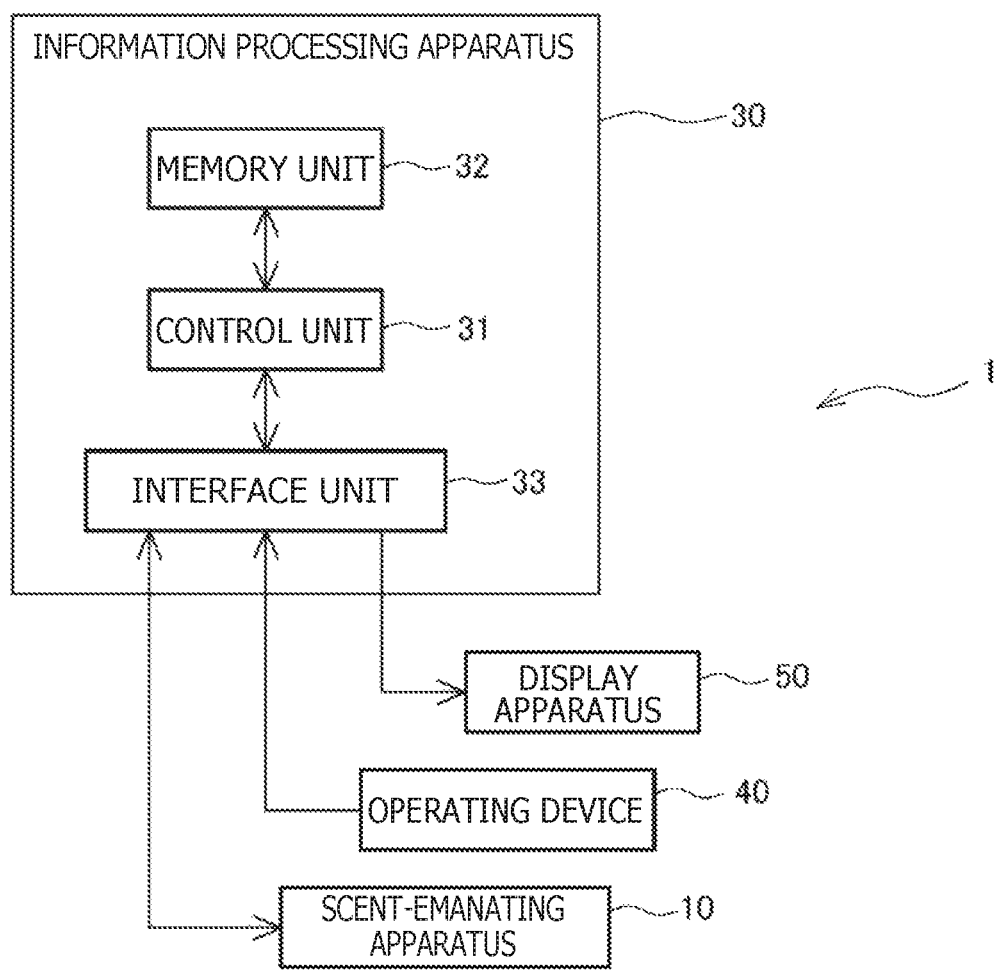
FIG. 1 is a block diagram depicting a structure of a scent-emanating system including a scent-emanating apparatus according to one embodiment of the present invention.

FIG. 1 is a block diagram depicting the structure of a scent-emanating system 1 including a scent-emanating apparatus 10 according to one embodiment of the present invention. As illustrated in FIG. 1, the scent-emanating system 1 includes the scent-emanating apparatus 10, an information processing apparatus 30, an operating device 40, and a display apparatus 50.

The scent-emanating apparatus 10 is an apparatus which emanates a scent for a user. In other words, it discharges a scent substance (composed of scent molecules) into air so that the user smells a specific scent. According to this embodiment, the scent-emanating apparatus 10 is so constructed as to permit a cartridge 20 to be attached and detached. The cartridge 20 holds a specific fragrance that emits a scent for the user to smell.

Figure 2:
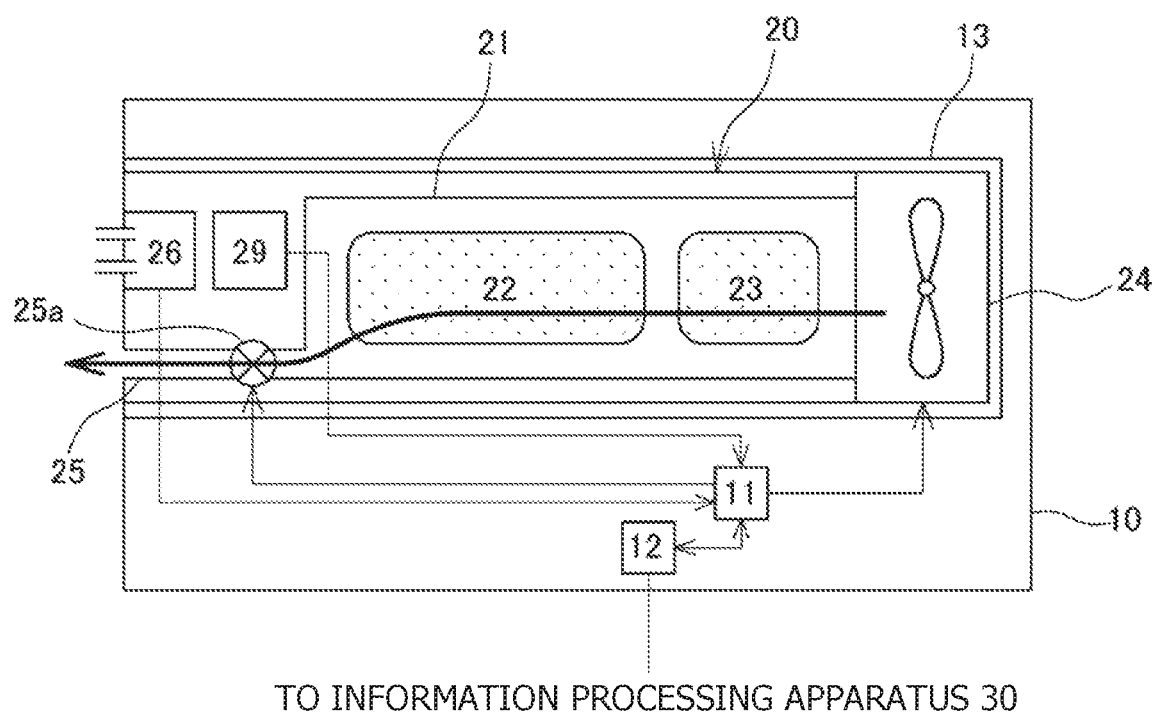
FIG. 2 is a schematic diagram depicting an example of a structure of the scent-emanating apparatus.

FIG. 2 is a schematic diagram depicting an example of the structure of the scent-emanating apparatus 10 which is provided with the cartridge 20. The main body of the scent-emanating apparatus 10 depicted in FIG. 2 includes a control circuit 11, an interface 12, and a cartridge holder 13 that holds the cartridge 20. The cartridge 20 includes a fragrance holder 21, a discharging mechanism 24, a discharge port 25, a discharge valve 25a, a gas sensor 26, and a memory 29. The fragrance holder 21 contains a fragrance 22 and a marking material 23.

The control circuit 11 receives instructions transmitted from the information processing apparatus 30 and responds to them, thereby outputting the control signals that activate the discharging mechanism 24 and the discharge valve 25a which are mounted in the cartridge 20. As the result, the scent-emanating apparatus 10 discharges a scent substance into the air from the fragrance 22 held in the cartridge 20. In addition, the control circuit 11 acquires the results of sensing by the gas sensor 26 (to be mentioned later) and sends them to the information processing apparatus 30. The interface 12 is intended to exchange information with the information processing apparatus 30 through a wire or wireless circuit. The control circuit 11 uses this interface 12 to receive instructions from the information processing apparatus 30 and to send the results of sensing by the gas sensor 26 to the information processing apparatus 30.

The fragrance holder 21 holds therein the fragrance 22 and the marking material 23. The fragrance holder 21 remains airtight until the cartridge 20 comes into use. To be more concrete, the fragrance holder 21 has the discharge port 25 that passes through the outer wall thereof. The disport port 25 remains closed by the discharge valve 25a until the cartridge 20 is put into use.

The fragrance 22 is a material that emanates a specific scent; for example, it may be any material that emanates a scent substrate upon volatilization. The fragrance 22 may be contained in the fragrance holder 21 in its liquid state (or impregnated into a porous material).

The marking material 23 is a substance that generates gaseous molecules to be detected by the gas sensor 26 (to be mentioned later). In what follows, the gaseous molecules generated by the marking material 23a will be referred to as "marker substance." The marker substance is different from the scent substance which the fragrance 22 generates. It should preferably be one which does not have a scent that can be sensed by the human. In addition, it should preferably be one which does not cancel the scent to be perceived by the human. The marking material 23 may be one which generates the marker substance upon volatilization in the same way as the fragrance 22; alternatively, it may be one which generates the marker substance upon chemical reactions or the like. The marker substance may be alcohol, carbon dioxide, or the like. Incidentally, FIG. 2 depicts an instance in which the fragrance 22 and the marking material 23 are held separately in the fragrance holder 21; however, this is not mandatory and they may be held together in a mixed state.

The discharging mechanism 24 is intended to make a gas flow, which moves from the fragrance holder 21 toward the discharge port 25, to be discharged outwards from the scent-emanating apparatus 10. The discharging mechanism 24 so works as to discharge the scent substance generated from the fragrance 22 and the marker substance generated from the marking material 23 outwards from the scent-emanating apparatus 10 through the discharge port 25. To be more concrete, the discharging mechanism 24 may be a fan or blower. The discharging mechanism 24 should preferably be one which is able to control the strength of the gas flow it generates. The controlled gas flow helps adjust the amount of the scent substance discharged per unit time by the scent-emanating apparatus 10, thereby changing the intensity of the scent perceived by the user. Incidentally, FIG. 2 includes an arrow of solid line which indicates the direction of the gas flow generated by the discharging mechanism 24.

The discharging mechanism 24 has the discharge port 25, which is a gas passage penetrating the fragrance holder 21. The discharge port 25 permits the scent substance and marker substance to be discharged outwards from the scent-emanating apparatus 10. The discharging mechanism 24 also has the discharge valve 25a, which is arranged between the fragrance holder 21 and the discharge port 25; it opens and closes in response to the control signal from the control circuit 11. The discharge valve 25a opens when the discharging mechanism 24 is in operation, thereby allowing the scent substance and marker substance to be discharged into the air from the fragrance holder 21. Also, the discharge valve 25a closes when the discharging mechanism 24 is idle, thereby preventing the scent substance and marker substance from leaking outwards from the scent-emanating apparatus 10. Incidentally, the discharge valve 25a should preferably be one which is of the normally-closed type that automatically closes when the power supply is suspended. The discharge valve 25a is described above as the one which is electrically opened and closed in response to the control signal from the control circuit 11; however, it is not restricted to that but may be a check valve which is automatically opened by the pressure which occurs when the discharging mechanism 24 becomes active and is automatically closed while the discharging mechanism 24 is idle. In this case, the check valve 25a operates without electric power supply.

The gas sensor 26 is arranged in the vicinity of the outlet of the discharge port 25; it detects the marker substance contained in the air outside the scent-emanating apparatus 10. Specifically, the gas sensor 26 according to this embodiment is intended to measure the amount (concentration) of the marker substance in the air. The gas sensor 26 may be a sensor of any type capable of detecting the marker substance in question. Even though any scent substance presents difficulties in the direct detection of its presence in the air or the measurement of its concentration in the air with the aid of its chemical characteristics, the scent substance discharged by the scent-emanating apparatus 10 can be indirectly recognized by detecting the marker substance discharged together with the scent substance. The information processing apparatus 30 checks the results of measurement by the gas sensor 26 to estimate the amount of the scent substance (or the intensity of generated scent) actually discharged from the scent-emanating apparatus 10.

The memory 29 may be a non-volatile memory or an identification (ID) tag; it stores the information about the cartridge in question 20. The information stored in the memory 29 is previously written in it prior to shipment of the cartridge. To be more concrete, the memory 29 stores the information about the type of the fragrance 22 and the marking material 23 contained in the cartridge 20, the producer of the cartridge 20, and the date of production and expiry of the cartridge 20. Such information may additionally contain the attributes, the properties and the usage conditions of the fragrance 22 (e.g., the intensity of scent and the use in combination with other fragrances). The information mentioned above is read out by the control circuit 11 and transmitted to the information processing apparatus 30.

The information processing apparatus 30 may be any one of a domestic game machine, a portable game machine, a personal computer, a smart phone, a tablet, etc. As depicted in FIG. 1, the information processing apparatus 30 includes a control unit 31, a memory unit 32, and an interface unit 33.

The control unit 31 includes at least one processor (such as central processing unit (CPU)); it executes the program stored in the memory unit 32, thereby performing information processing variously. A detailed description will be given below of the processing which is performed by the control unit 31 according to this embodiment. The memory unit 32 includes at least one of memory devices such as random access memory (RAM); it stores the program to be executed by the control unit 31 and the data to be processed by the program.

The interface unit 33 is intended for communication to exchange a variety of data with the scent-emanating apparatus 10, the operating device 40, and the display apparatus 50. The interface unit 33 allows the information processing apparatus 30 to be connected to any one of the scent-emanating apparatus 10, the operating device 40, and the display apparatus 50 through a wire or wireless circuit.

The operating device 40 is intended to accept the input of operation from the user. It sends the received signal (denoting the content of the user's operation) to the information processing apparatus 30. Incidentally, the operating device 40 may be a controller or keyboard connected to the household game machine; it may additionally include buttons arranged on the enclosure of the information processing apparatus 30.

The display apparatus 50 may be an organic electroluminescence (EL) display or a liquid-crystal display; it has a screen that displays videos in response to the video signals received from the information processing apparatus 30. The display apparatus 50 may also be a head-mount display (which is a device which the user wears on his or her head). Moreover, the display apparatus 50 may be configured integrally with the enclosure of the information processing apparatus 30.

In addition, the scent-emanating apparatus 10 may be integrally configured with the information processing apparatus 30, the operating device 40, and display apparatus 50 arranged in the enclosure. In the case where the display apparatus 50 is of headgear type, the scent-emanating apparatus 10 built into the enclosure of the display apparatus 50 permits the scent substance to be discharged close to the user's nose.

The following is a detailed description of the process to be executed by the information processing apparatus 30. The information processing apparatus 30 has the control unit 31 which executes the program stored in the memory unit 32, thereby realizing the step of emanating the scent to the user.

For example, the control unit 31 executes the application program such as game. In this case, the control unit 31 provides the scent-emanating apparatus 10 with an instruction to emanate the scent to the user when a specific object appears in the game as the game proceeds. The following description uses a term "instruction to emanate the scent" which means that the control unit 31 transmits the instruction to cause the scent-emanating apparatus 10 to emanate the scent.

It is assumed in this embodiment that the instruction to emanate the scent includes a parameter (called scent intensity value hereinafter) that specifies the scent intensity in response to the instruction to emanate the scent. Upon receipt of the instruction to emanate the scent, the scent-emanating apparatus 10 opens the discharge valve 25a and activates the discharging mechanism 24 in response to the scent intensity value included in the instruction to emanate the scent. In other words, the scent-emanating apparatus 10 causes the control circuit 11 to work such that the discharging mechanism 24 emanates the scent at a specific gas flow rate in response to the scent intensity value. In this way, the scent-emanating apparatus 10 gives the user the scent which has a certain intensity in response to the instruction from the information processing apparatus 30.

In addition, the control unit 31 sends the instruction to emanate the scent to the scent-emanating apparatus 10 and then acquires from the scent-emanating apparatus 10 the data representing the amount of the marker substance which has been measured by the gas sensor 26. In answer to the result of measurement, the control unit 31 sends signals that instruct the scent-emanating apparatus 10 to emanate the scent. To be more concrete, in the case where the amount of the marker substance, which has been discharged in response to the first instruction to emanate the scent, is less than the expected value, the control unit 31 sends another instruction to emanate the scent that specifies the scent intensity value higher than that given before. Conversely, in the case where the measured amount of the marker substance is more than the expected value, the control unit 31 may send an instruction to stop emanating the scent. Alternatively, in the case where the instruction to emanate the scent continues, the control unit 31 may send an instruction to emanate the scent with a lower scent intensity value than that in the previous stage. The expected value for the result of measurement may be a value which has been previously established in correspondence to the scent intensity value specified by the previous instruction to emanate the scent. Moreover, the control unit 31 may cause the scent-emanating apparatus 10 to send the instruction to emanate the scent, during which it periodically repeats the feedback control. Thus, the control unit 31 will be able to maintain the desirable scent intensity for the scent which is actually emanated for the user.

Figure 3:
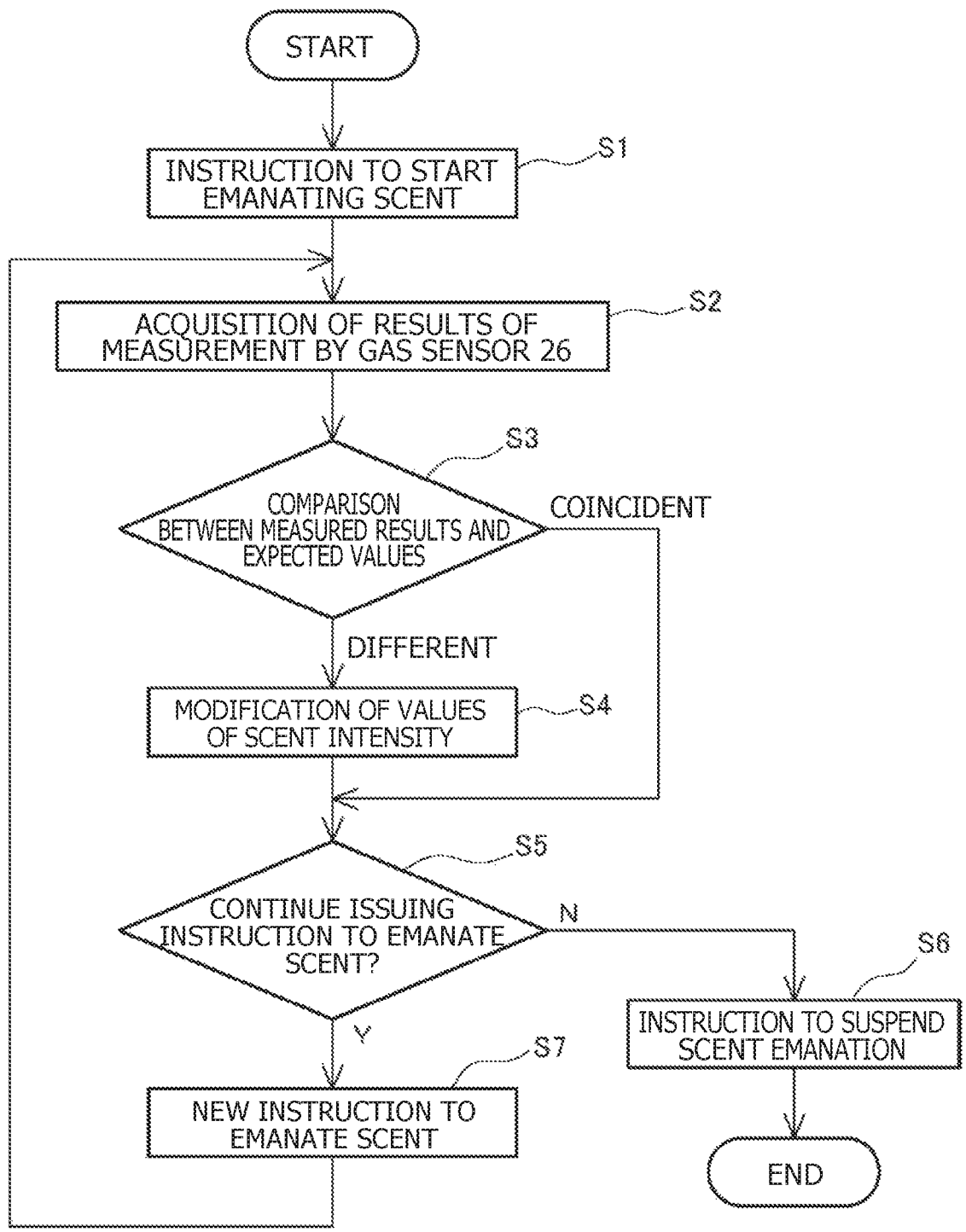
FIG. 3 is a flowchart depicting an example of a process to be executed by an information processing apparatus.

The control unit 31 mentioned above performs the feedback control according to the flow chart depicted in FIG. 3. At the start, the control unit 31 sends an instruction to emanate the scent (or to start the scent-emanating stage) in coincidence with timing at which the object as the origin of scent appears in the game (S1). The instruction to emanate the scent includes the value for scent intensity which is determined in response to the parameter in the game and the distance between the user's character and the object. After that, the scent-emanating apparatus 10 starts to emanate the scent in response to the instruction in S1 and then it sends the results of measurement by the gas sensor 26 to the information processing apparatus 30. The control unit 31 acquires the result of measurement by the gas sensor 26 which has been sent from the scent-emanating apparatus 10 (S2).

Subsequently, the control unit 31 compares the results of measurement by the gas sensor 26 with the expected value (S3). The expected value is one which is determined in response to the value of the intensity of the scent as indicated in the instruction to emanate the scent in S1. In the case where the difference between the results of measurement by the gas sensor 26 and the expected value is within a prescribed threshold value, the control unit 31 determines that the results of measurement coincides with the expected value, and it proceeds to S5. In the case where the results of measurement are different from the expected value (or larger than the threshold value), the control unit 31 modifies, in response to the result of comparison, the value of scent intensity to be included in the subsequent instruction to emanate the scent (S4). To be more concrete, if the result of measurement by the gas sensor 26 is lower than the expected value, the value of scent intensity is increased; otherwise, the value of scent intensity is decreased.

Subsequently, the control unit 31 determines whether or not to continue issuing the instruction to emanate the scent (S5). That is, the control unit 31 sends a signal to the scent-emanating apparatus 10 so that the instruction to emanate the scent is suspended when the object in the game (which is the origin of scent) has disappeared or it has become unnecessary to continue emanating the scent (S6). Thus the step of emanating the scent comes to an end. On the other hand, in the case where it is necessary to continue sending the instruction to emanate the scent, the control unit 31 sends a new instruction to emanate the scent to the scent-emanating apparatus 10 (S7). The new instruction to emanate the scent indicates the value of scent intensity which has been modified in S4. Subsequently, the control unit 31 returns to S2 in order to perform the feedback control. Incidentally, the expected value to be determined in response to the value of scent intensity contained in the instruction to emanate the scent in S7 is used at the time of comparison (to be made in S3) between the expected value and the result of measurement by the gas sensor 26. In this way, the control unit 31 repeats the steps of correcting the value of scent intensity according to the results of measurement by the gas sensor while the scent is being emanated. This procedure makes it possible to maintain desirable values for the scent intensity of the scent being actually emanated for the user.

The control unit 31 may also send a new control instruction to immediately suspend emanating the scent if the result of measurement exceeds the prescribed limit value regardless of the value of scent intensity which has been specified in the previous instruction to emanate the scent. This procedure makes it possible to suspend emanating the scent when the scent with an exceedingly high scent intensity is emanated.

In addition, the control unit 31 is able to utilize the results of measurement by the gas sensor 26, thereby predicting when to replace the cartridge 20. The cartridge 20 contains the fragrance 22 and the marking material 23, which gradually decrease as the scent-emanating apparatus 10 repeats the step of emanating the scent. This leads to a decrease in the amount of scent substance to be emanated. Thus, the control unit 31 determines that the fragrance 22 and the marking material 23 are becoming short when it finds that the result of measurement by the gas sensor 26 is lower than the prescribed value after it has sent the instruction to emanate the scent. In this case, the control unit 31 causes the display apparatus 50 to display a message to urge the replacement of the cartridge 20 or causes a predetermined indicator lamp (arranged on the enclosure of the scent-emanating apparatus 10) to light, thereby informing the user that the cartridge 20 needs replacement. Alternatively, the control unit 31 may be so designed as to be able to estimate the residual quantity of the fragrance 22 according to the result of measurement by the gas sensor 26 and to display the estimated residual quantity.

Incidentally, it is not necessarily true that the fragrance 22 and the marking material 23 in the cartridge 20 are consumed at a constant rate. Therefore, it is desirable that the cartridge 20, at the time of its shipment, be filled with the fragrance 22 and the marking material 23 in such a way that the latter is consumed faster than the former. (In other words, the amount of the marking material 23 is smaller than that of the fragrance 22.) In this way, it is possible to avoid the situation in which the fragrance 22 becomes short before the gas sensor 26 becomes unable to detect the marker substance.

The control unit 31 is also capable of detecting the unexpected leakage of the scent substance with the help of measurement result by the gas sensor 26. The gas sensor 26 detects the marker substance existing in the atmospheric air outside the discharge port 25. Therefore, in the case where the gas sensor 26 detects the presence of the marker substance in an amount equal to or higher than the prescribed level before the control unit 31 sends an instruction to emanate the scent, it suggests the possible leakage of the scent substance and marker substance from the cartridge 20 through the discharge port 25a. In order to cope with this situation, the control unit 31 acquires the results of measurement by the gas sensor 26 at an appropriate timing (e.g., when the information processing apparatus 30 starts) before it sends the instruction to emanate the scent. And, the control unit 31 informs the user about the possibility of gas leakage or suspends the action of the scent-emanating apparatus 10 if the result of measurement is found higher than the prescribed value.

Incidentally, even though the gas sensor 26 does not have the function to measure the amount of the marker substance, the control unit 31 can detect the shortage of the fragrance 22 left unused or detect the leakage of the scent substance so long as the gas sensor 26 is able to detect the presence or absence of the marker substance. To be more concrete, if it is assumed that the gas sensor 26 is able to detect the presence of the marker substance (in an amount equal to or more than the prescribed level) in the air, the control unit 31 determines that the amount of the fragrance 22 remaining unused is lower than the prescribed level in the case where it does not detect the presence of the marker substance after it has sent the instruction to emanate the scent 22. It also determines that there is a gas leakage in the case where it detects the presence of the marker substance before it has sent the instruction to emanate the scent 22.

The control unit 31 may also determine whether or not the cartridge 20 is available with the help of the information about the production date and expiration date which is stored in the memory 29 in the cartridge 20. To be more concrete, the control unit 31 will send the instruction not to use the cartridge 20 or the instruction to tell the user the necessity for replacement of the cartridge 20 in the case where the expiration date (stored in the memory 29) has come. The control unit 31 may also be regulated such that it does not use the cartridge 20 which has passed for a certain period after the production date stored in the memory 29. The control unit 31 may also be designed such that it refers to the information read out from the memory 29 so as to check to see if the cartridge 20 is the legitimate one. If the result of checking indicates that the cartridge 20 mounted on the scent-emanating apparatus 10 is not the legitimate one, the control unit 31 sends the instruction not to emanate the scent by using the cartridge in question. The control unit 31 reads out the information stored in the memory 29 when the scent-emanating apparatus 10 is put into use or the cartridge 20 is replaced by a new one; this procedure permits the control unit 31 to determine whether or not it can use the cartridge 20 in question.

As explained above, the scent-emanating apparatus 10 pertaining to this embodiment has the fragrance holder 21 which holds the fragrance 22 together with the marking material 23; this configuration permits the scent-emanating apparatus 10 to emanate the marker substance at the same time as the scent substance is discharged. In addition, the gas sensor 26 detects the marker substance in the air so that the information processing apparatus 30 can know whether or not the scent substance is being discharged or know the amount of the scent substance being discharged even in the case where it is difficult to directly detect the scent substance. The result of such checking and detection permits the scent-emanating apparatus 10 to work adequately or to provide the user with the information about its state.

The foregoing description is based on an assumption that the scent-emanating apparatus 10 has the removable cartridge 20 which holds the fragrance 22 and the marking material 23; however, the scent-emanating apparatus 10 may be that of throwaway type. In this case, the constituents contained in the cartridge 20 as mentioned above will be built directly into the scent-emanating apparatus 10.

Figure 4:
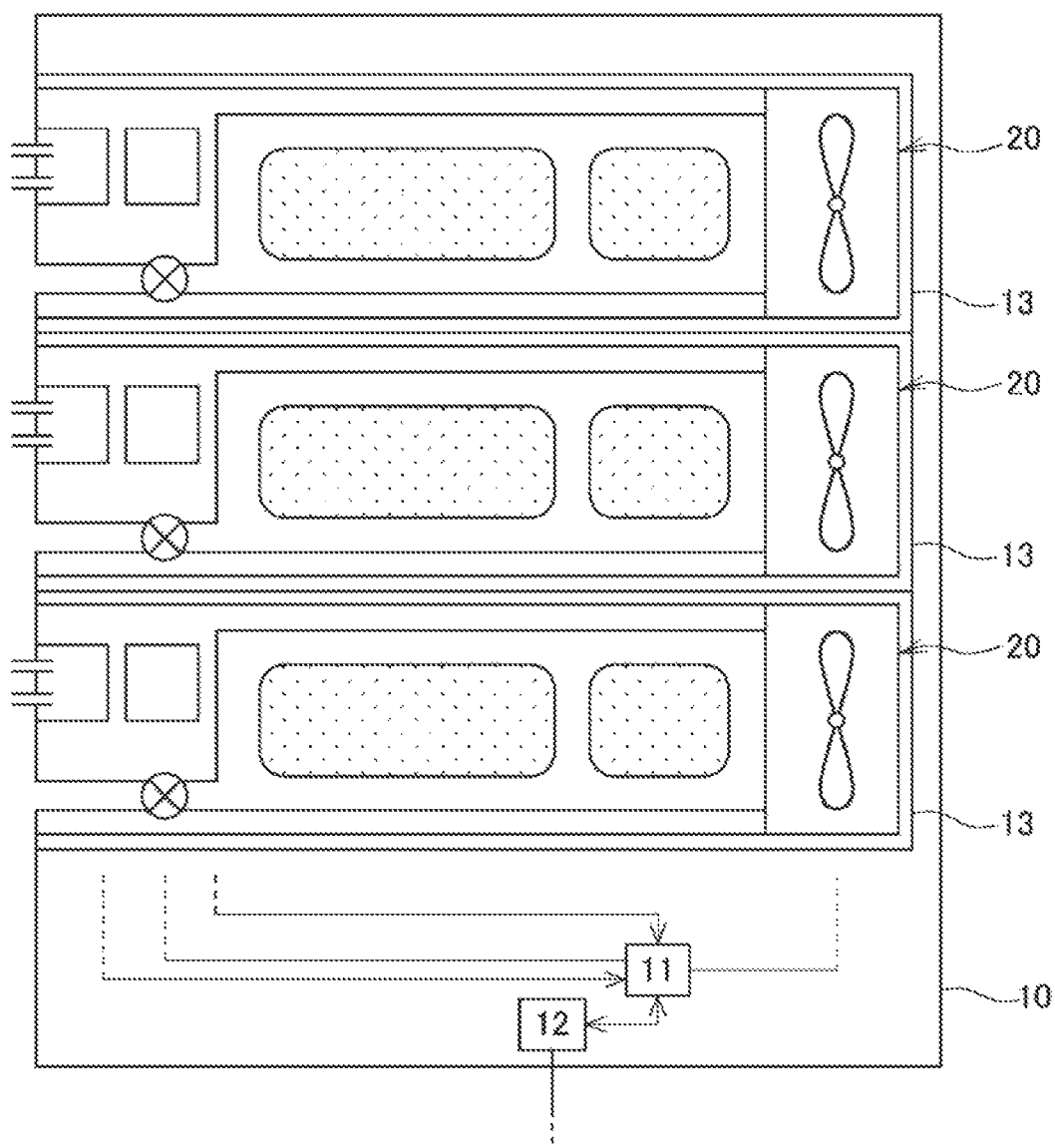
FIG. 4 is a schematic diagram depicting an example of the structure of the scent-emanating apparatus that can be provided with a plurality of cartridges.

Moreover, the scent-emanating apparatus 10 may be constructed such that the cartridge 20 is replaced by more than one of removable type. The scent-emanating apparatus 10 constructed in this manner will be able to emanate more than one kind of scent. FIG. 4 depicts an example of the structure of the scent-emanating apparatus 10 constructed as mentioned above. The illustrated scent-emanating apparatus 10 has three built-in cartridges 20. The control circuit 11 for the scent-emanating apparatus 10 is able to control individually the discharging mechanism 24 and the discharge port 25a of the cartridges 20. The information processing apparatus 30 causes the control unit 31 to send the instruction to specify the cartridge 20 from which the scent is emanated. The scent-emanating apparatus 10 opens the discharge valve 25a for the specified cartridge 20 and activates the discharging mechanism 24 for the specific cartridge 20, so that the fragrance 22 (scent substance) emanates from the specified cartridge 20. Incidentally, according to this embodiment, the information processing apparatus 30 causes the control unit 31 to reference the information which has been read out from the memory 29 built in the respective cartridges 20, thereby specifying the fragrance 22 contained in each cartridge 20.

In the forgoing case, the marking materials 23 contained in the individual cartridges 20 may be identical with or different from one another. In the case where the individual cartridges 20 contain the marking materials 23 of the same kind and several kinds of scent substances are emanated from more than one cartridge 20 at the same time, it would be difficult to estimate the amount of the scent substance being discharged from the individual cartridges 20. However, it would be possible to roughly estimate the total amount of the scent substance being emanated. Moreover, in the case where it is desirable for only one scent substance to be discharged at one time, it would be possible to estimate the amount of the discharged scent substance in question, if it is possible to acquire the result of detection by the gas sensor 26 which works during discharging.

On the other hands, in the case where the individual cartridges 20 contain the marking materials 23 differing from one another, each cartridge 20 is provided with the gas sensor 26 which is able to detect the marker substance discharged from the marking material 23 contained therein. In other words, the cartridges 20 of different kinds contain the fragrance 22 and the marking material 23 which are different from those contained in the cartridges 20 of different kind and the gas sensor 26 built therein detects the gases of different kind. The information processing apparatus 30 acquires the result of detection by the gas sensor 26 built in the individual cartridges 20, thereby roughly estimating the amount of the scent substance being discharged from the individual cartridges 20. Thus, it is able to estimate the amount of the scent substances individually even in the case where the scent substance is discharged from more than one cartridge 20 at the same time.

Incidentally, the structure mentioned above may be modified such that the elements built in the cartridge 20 are partly built in the main body of the scent-emanating apparatus 10. For example, in the case where the marking materials 23 of the same kind are contained in the individual cartridges 20, it is only necessary for the gas sensor 26 to detect one kind of the marker substance, and hence the constituent in question may be mounted in the main body of the scent-emanating apparatus 10 instead of the individual cartridges 20.

Moreover, the scent-emanating apparatus 10 may be so constructed as to have a deodorizing mechanism that deodorizes the scent which has been emanated therefrom. For example, in the event that an object which generates a specific scent appears in the game, it would be possible to enhance the ambiance if the scent-emanating apparatus 10 discharges the specific scent. However, the ambiance would be impaired if the scent emanated from the scent-emanating apparatus 10 remains after the object has disappeared or the user's character has left the object. This situation would be avoided if the scent which has been emanated and become useless is deodorized so that the user does not perceive that scent. The deodorizing mechanism mentioned above would be realized in various ways. The following represents several examples of such deodorizing mechanisms which are built into the cartridge 20.

Figure 5:
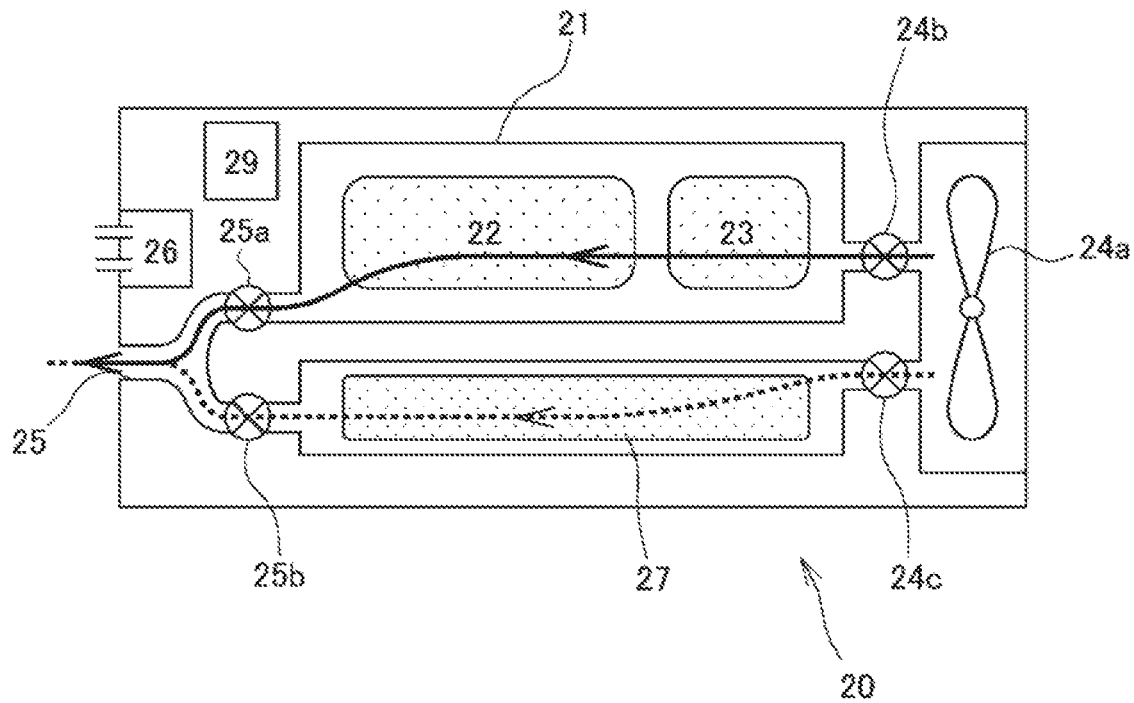
FIG. 5 is a schematic diagram depicting an example of a structure of a cartridge provided with a deodorizing mechanism.

FIG. 5 depicts an example of the structure of the cartridge 20 provided with the deodorizing mechanism that discharges a deodorant 27 to deodorize the scent. In this example, the deodorant 27 is contained in the space isolated from the fragrance holder 21 in the cartridge 20. Moreover, in this example, it is assumed that the discharging mechanism 24 generates air flows independently for the individual spaces each holding the fragrance holder 21 and the deodorant 27. This mechanism may be realized with two independent fans or one fan combined with a plurality of valves that switch the paths for the air flow generated by the fan.

In the case of the example depicted in FIG. 5, it is assumed that the discharging mechanism 24 is realized with one fan 24a and two valves 24b and 24c. The valve 24b is arranged between the fragrance holder 21 and the fan 24a; it opens when the scent-emanating apparatus 10 emanates the scent, and it remains closed otherwise. The valve 24c is arranged between the space (in which is contained the deodorant 27) and the fan 24a; it opens when the scent-emanating apparatus 10 performs deodorizing, and it remains closed otherwise. Incidentally, as in the case of the discharge valve 25a, the valves 24b and 24c may be those which are actuated in response to the control signal from the control circuit 11 or may be check valves capable of opening and closing automatically in response of the difference in atmospheric pressure.

In order to achieve deodorizing, the scent-emanating apparatus 10 activates the discharging mechanism 24, thereby discharging the deodorant 27 outwards. For this purpose, the deodorant 27 may be discharged through the passage a part of which is used in common with the fragrance 22 and the marking material 23. To be more concrete, the deodorant 27 may be discharged outwards from the scent-emanating apparatus 10 through the discharge port 25 as in the case of the fragrance 22. In this case, another valve 25b (which is different from the discharge value 25a) is arranged between the space (in which is contained the deodorant 27) and the discharge port 25; it is opened when deodorizing is performed. The shared use of the discharge port 25 permits the deodorant 27 to effectively deodorize the scent substance discharged from the discharge port 25. In this case, a provision should be made so that the marker substance is also absorbed by the deodorant 27 without reaction with the gas sensor 26. Incidentally, the broken line arrow in the diagram denotes the gas flow which is produced by the fan 24a at the time of deodorizing.

The information processing apparatus 30 causes the control unit 31 to send the instruction to emanate the scent and then send the instruction to deodorize to the scent-emanating apparatus 10 at the time of terminating the scent emanation. In response to this instruction, the scent-emanating apparatus 10 causes the control circuit 11 to activate the discharging mechanism 24 for the deodorant 27 to be discharged. The result is that the scent which has been emanated is deodorized instantly so that it is not perceived by the user any longer.

A further provision may be made such that the control unit 31 sends the deodorizing instruction and then acquires the result of measurement by the gas sensor 26. Thus the control unit 31 sends an instruction to cause the scent-emanating apparatus 10 to continue discharging the deodorant 27 while the result of measurement remains higher than the prescribed value and to suspend the deodorizing step when the result of measurement decreases below the prescribed value. Thus the result of measurement by the gas sensor 26 is used for feedback control at the time of emanating the scent as well as at the time of deodorizing; the process in this way continues the deodorizing step until the marker substance (which has been discharged together with the scent substance) disappears from the vicinity of the discharge port 25. This ensures the deodorizing step.

Incidentally, the example shown above is designed such that one fan 24a is activated at the time when the scent is emanated as well as at the time when deodorizing is performed. This design may be replaced by the one in which the cartridge 20 is provided with separate fans, one for scent emanating and one for deodorizing. In this case, the fans are activated individually so as to discharge the scent substance, the marker substance and the deodorant 27.

Figure 6:
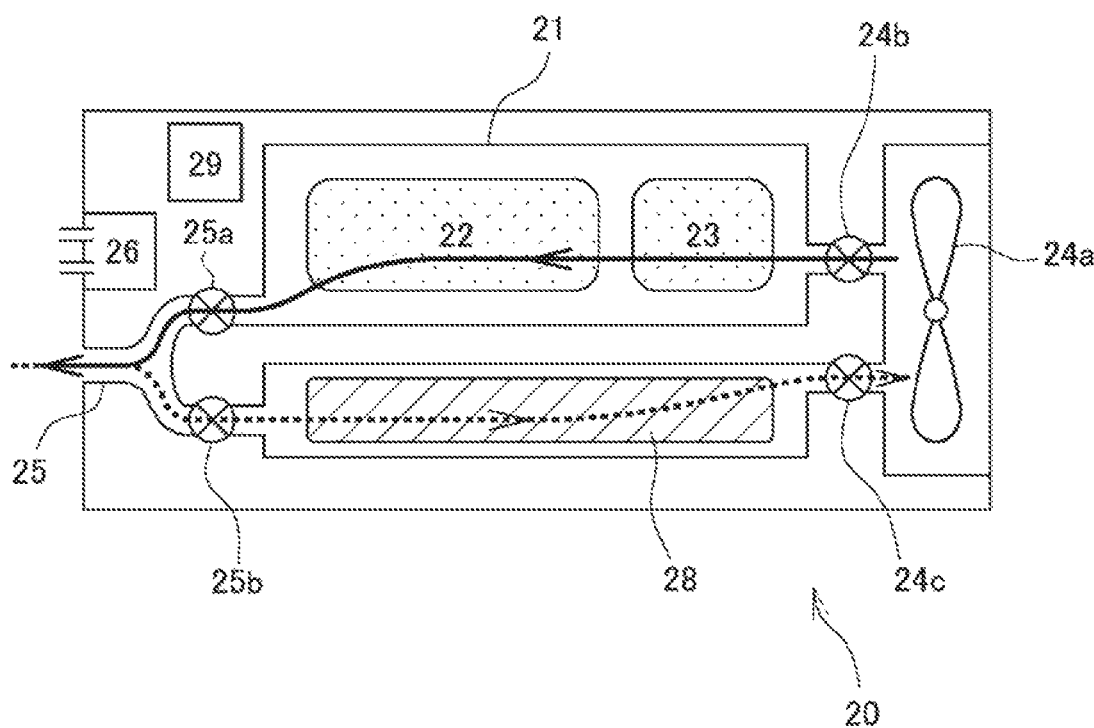
FIG. 6 is a schematic diagram depicting another example of the structure of the cartridge provided with a deodorizing mechanism.

FIG. 6 depicts the structure of the cartridge 20 which is so constructed as to perform deodorizing by suction (instead of emission as depicted in FIG. 5). In this example, the deodorant 27 depicted in FIG. 5 is replaced by a deodorizing filter 28. Also, as in the case depicted in FIG. 5, the valve 25b is arranged between the space (in which is contained the deodorizing filter 28) and the charging port 25, and the valve 24c is arranged between the space (in which is contained the deodorizing filter 28) and the fan 24a.

In this example, the process of discharging the scent substance is accomplished in the following way. The scent-emanating apparatus 10 opens the discharging valve 25a and the valve 24a and activates the fan 24a, thereby generating the gas flow that moves outwards from the cartridge 20 as in the case depicted in FIG. 5. On the other hand, in the case of the deodorizing process, the scent-emanating apparatus 10 opens the valves 25b and 24c and activates the fan 24a in the opposite direction for suction. This process causes the cartridge 20 to suck the air (outside the scent-emanating apparatus 10) through the discharge port 25, as indicated by the broken line arrow in the diagram. The sucked air passes through the space in which is arranged the deodorizing filter 28. At this time, the deodorizing filter 28 absorbs the scent substance to achieve the deodorizing process. As mentioned above, the embodiment depicted in FIG. 6 is designed to perform the deodorizing process by sucking the outside air unlike the embodiment depicted in FIG. 5.

Incidentally, the embodiment mentioned above may employ the valves 24b and 24c which are check valves (like those depicted in FIG. 5) which automatically open and close in response to the difference in atmospheric pressure. However, in the case depicted in FIG. 6, the valve 24c is arranged oppositely to that depicted in FIG. 5, so that it opens when the gas flows in the direction from the deodorizing filter 28 to the fan 24a. Incidentally, as in the case where the deodorant 27 is employed, in the case where the deodorant filter 28 is employed, it may be possible to install a fan that sucks air at the time of deodorizing process in addition to the fan 24a which works when the scent is emanated.

The embodiments depicted in FIGS. 5 and 6 are designed such that each of the cartridges 20 is provided with the deodorizing mechanism; however, they may be modified such that the deodorizing mechanism is attached to the main body of the scent-emanating apparatus 10. They may also be modified such that a deodorizing cartridge (which contains the deodorant 27 or the deodorizing filter 28) is provided in addition to the cartridge 20 containing the fragrance 22 and this cartridge is mounted on the scent-emanating apparatus 10.

The embodiment mentioned above is designed such that the fan (or the similar mechanism) generates the gas flow which discharges outwards the scent substance and marker substance from the scent-emanating apparatus 10. The scent-emanating apparatus 10 is not restricted to that mentioned above; it may be modified such that it discharges the scent substance and marker substance in varied ways. For example, in the case where the cartridge 20 contains the fragrance 22 in liquid form, the cartridge 20 may have a built-in vaporizing device as a part of the discharging mechanism 24. In this case, the scent-emanating apparatus 10 activates this vaporizing device when the scent is emanated, so that the scent-emanating apparatus 10 discharges outwards the scent substance which is generated as the scent 22 vaporizes. In addition, the scent-emanating apparatus 10 may cause the vaporizing device to work in combination with the blowing mechanism mentioned above, thereby discharging the scent substance. In any case, the scent-emanating apparatus 10 is so controlled as to discharge the marker substance, too, whenever it discharges the scent substance. This makes it possible to estimate the discharged amount of the scent substance by measuring the amount of the marker substance.

Modified Embodiments

As mentioned above, the scent-emanating apparatus 10 is able to discharge the scent substance and marker substance in various ways. The following is a description of the modified embodiments relating to the mechanism for discharging the scent substance and marker substance. Incidentally, the following description applies the same codes or symbols as used above to the constituents having the identical functions mentioned above. Moreover, the following description of the modified embodiments emphasizes the structure of the cartridge 20 which is intended to discharge the scent substance and the marker substance, and it is not accompanied by the diagrams depicting the fragrance 22 and the marking material 23 (which are contained in the fragrance holder 21) and the gas sensor 26.

Figure 7A:
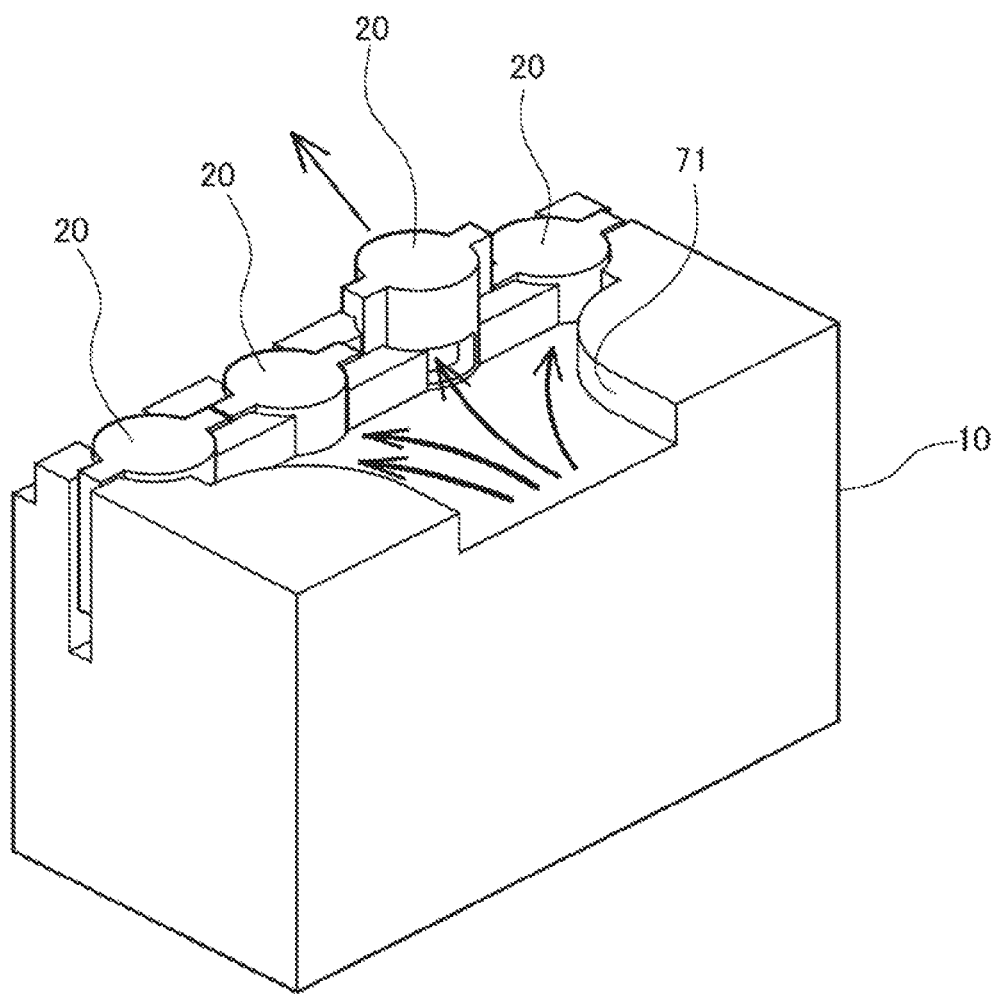
FIG. 7A is a perspective view depicting an external appearance of the scent-emanating apparatus pertaining to a first modified example.
Figure 7B:
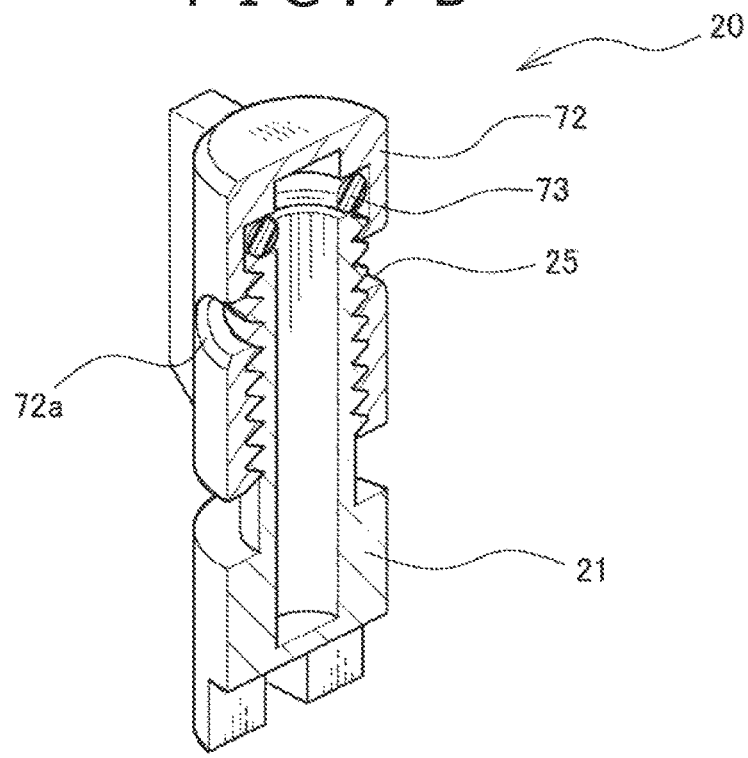
FIG. 7B is a cutaway perspective view depicting an unused cartridge pertaining to the first modified example.
Figure 7C:
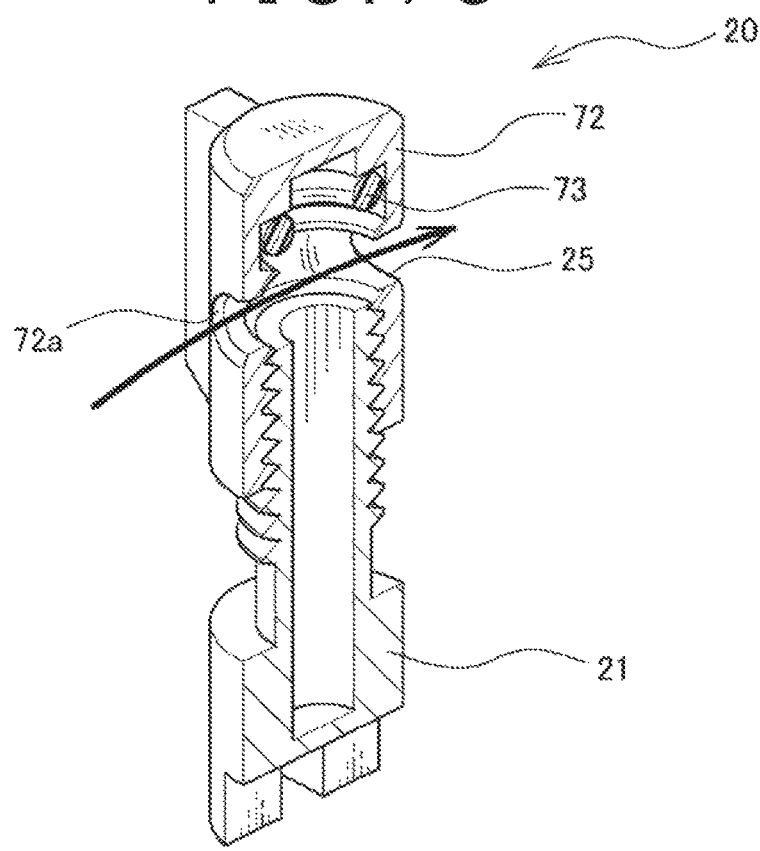
FIG. 7C is a cutaway perspective view depicting the cartridge at the time of emanating a scent pertaining to the first modified example.

The first modified embodiment, which employs ball screws, is described with reference to FIGS. 7A, 7B, and 7C. FIG. 7A is a perspective view depicting the outline of the scent-emanating apparatus 10 employed in the modified embodiment. FIGS. 7B and 7C are broken perspective views depicting the structure of the cartridge 20. FIG. 7A depicts that the modified embodiment has the scent-emanating apparatus 10 on which four cartridges 20 are mounted. The scent-emanating apparatus 10 has its main body support one fan (not depicted), which generates a gas flow through a passage 71 in the scent-emanating apparatus 10 by activating the fan. The gas flows generated by the fan move in the direction indicated by the arrows in the diagram. At the time of actual operation, the passage 71 has its top covered with a lid, so that the gas flow is introduced to the opening of the cartridge 20.

As depicted in FIGS. 7B and 7C, the cartridge 20 includes the fragrance holder 21, a cap 72, and an O-ring 73. As in the case of the embodiment depicted in FIG. 2, the fragrance holder 21 contains the fragrance 22 and the marking material 23. In the case of this modified embodiment, the fragrance holder 21 is formed approximately in a cylindrical shape, and it contains the fragrance 22 and the marking material 23 impregnated into a porous material in cylindrical form. The cap 72 and the fragrance holder 21 constitute a ball screw, with the cap 72 functioning as a nut and the fragrance holder 21 as a screw shaft. In addition, the fragrance holder 21 is connected to the motor in the main body when the cartridge 20 is mounted in the scent-emanating apparatus 10. The cap 72 has on its side wall two openings facing each other, one functioning as an inlet 72a and the other functioning as the discharge port 25. The O-ring 73 is fixed to the inner uppermost part in the cap 72.

The fragrance holder 21 is connected to the rotating shaft of the motor in the main body of the scent-emanating apparatus 10, so that it is rotated by the motor. This rotary action causes the cap 72 to move upwards or downwards. The rotary action by the fragrance holder 21 moves the cap 72 downwards. As the fragrance holder 21 advances to the uppermost part of the cap 72, its end comes into contact with the O-ring 74 as depicted in FIG. 7B. In this state, the inlet 72a and the discharge port 25 are closed by the side wall of the fragrance holder 21 and the gap between the cap 72 and the fragrance holder 21 is sealed by the O-ring 73, so that the fragrance holder 21 has its inside tightly closed. The cartridge 20 assumes this state when it is not yet used. This state corresponds to the state in which the discharge port 25a remains closed as depicted in FIG. 2.

At the time of emanating the scent, the scent-emanating apparatus 10 rotates the motor which is joined to the cartridge 20 holding the scent to be emanated. As the result, the fragrance holder 21 rotates and the cap 72 moves upwards. The cartridge 20 in the resulting state is depicted in FIG. 7C. In this state, the inlet 72a and the discharge port 25 (which face each other) open, thereby forming the gas passage in the cartridge 20. As the scent-emanating apparatus 10 activates the fan in this state, the gas flows into the cartridge 20 from the inlet 72a through the passage 71 and discharges from the scent-emanating apparatus 10 through the discharge port 25. The gas flow is indicated by the arrow in FIG. 7C. The gas being discharged from the discharge port 25 contains the scent substance and the marker substance.

Figure 8A:
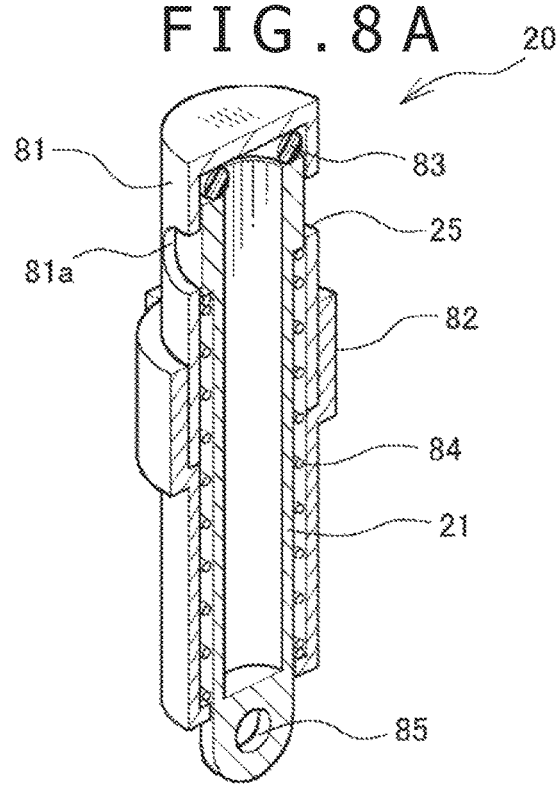
FIG. 8A is a cutaway perspective view depicting an unused cartridge pertaining to a second modified example.
Figure 8B:
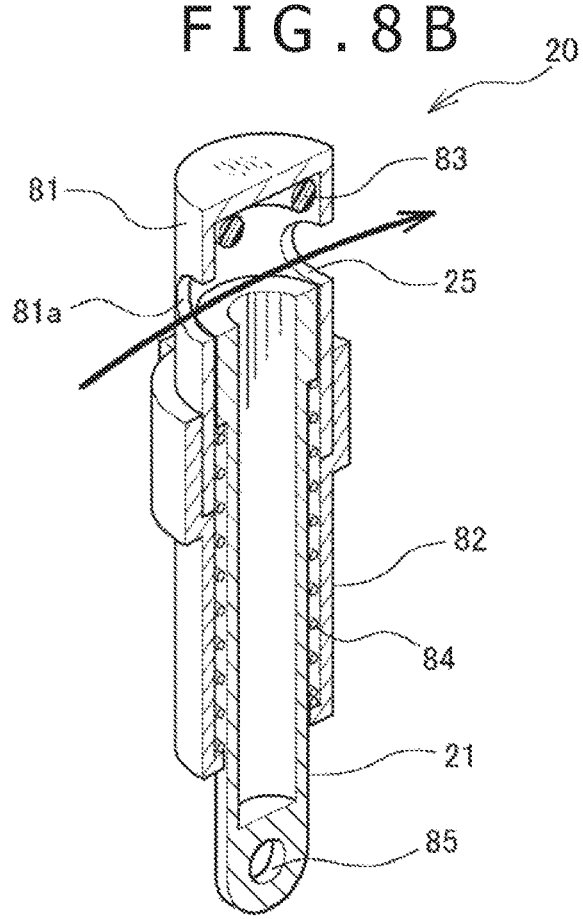
FIG. 8B is a cutaway perspective view depicting the cartridge at the time of emanating a scent pertaining to the second modified example.

The following is a description of the second modified embodiment which is provided with a direct acting actuator. FIGS. 8A and 8B are broken perspective views depicting the structure of the cartridge 20 employed in the second modified embodiment. This modified embodiment is characterized in that the cartridge 20 includes the fragrance holder 21, a cap 81, an outer shell 82, an O-ring 83, and a coil spring 84. As in the case of the first modified embodiment mentioned above, the fragrance holder 21 takes on a nearly cylindrical form and it contains the fragrance 22 and the marking material 23. The cap 81 has in its side wall two openings (an inlet 81a and the discharge port 25) facing each other. The cap 81 has the O-ring 83 at its inner uppermost position. The coil spring 84 is arranged between the fragrance holder 21 and the outer shell 82 in such a way as to surround the side wall of the fragrance holder 21 and energize the fragrance holder 21 upwards.

The second modified embodiment is characterized in that the fragrance holder 21 has a hole 85 at its lower end and the main body of the scent-emanating apparatus 10 has a built-in direct acting actuator which is joined to a hook. In order for the scent-emanating apparatus 10 to emanate the scent, the hook is engaged with the hole 85 and the direct acting actuator is put to action. This process causes the fragrance holder 21 to be pulled down so that the inlet 81a and the discharge port 25 open as depicted in FIG. 8B. In this state, the fan attached to the main body of the scent-emanating apparatus 10 is actuated as in the case of the first modified embodiment that employs the ball screw. This action brings about the gas flow which enters the cartridge 20 from the inlet 81a and moves outwards from the scent-emanating apparatus 10 through the discharge port 25. The gas being discharged from the discharge port 25 contains the scent substance and marker substance as in the case of the first modified embodiment. In the case where the scent is not emanated, the hook is disengaged from the hole 85 so that the fragrance holder 21 is energized upwards by the action of the coil spring 84. As the result, the inlet 81a and the discharge port 25 are closed as depicted in FIG. 8A.

The first and second modified embodiments mentioned above obviate the necessity of mounting the blowing mechanism on each cartridge 20. One blowing mechanism built in the main body of the scent-emanating apparatus 10 is enough to cause any one of the cartridges 20 to discharge the desired scent.

Figure 9A:
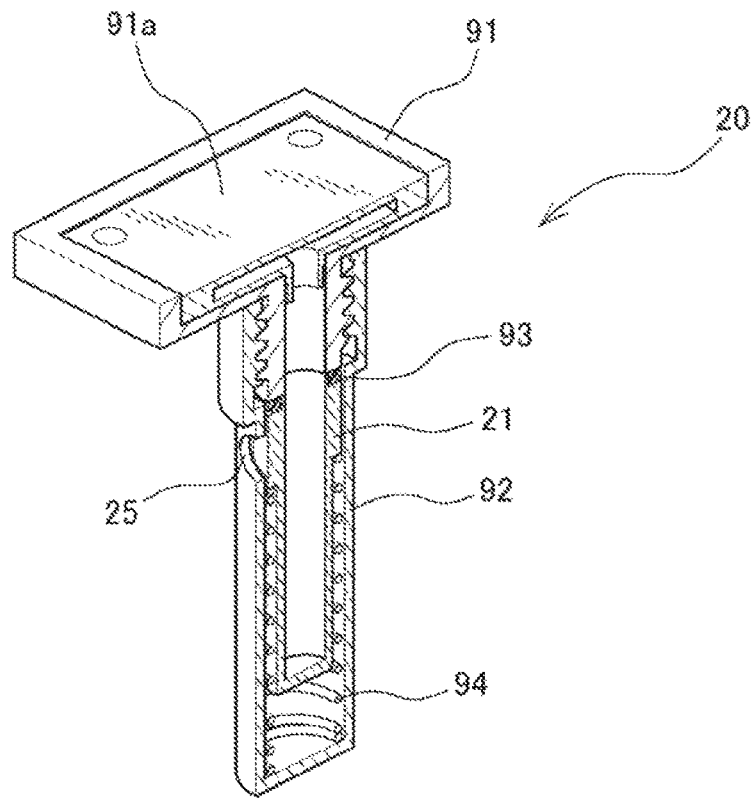
FIG. 9A is a cutaway perspective view depicting an unused cartridge pertaining to a third modified example.
Figure 9B:
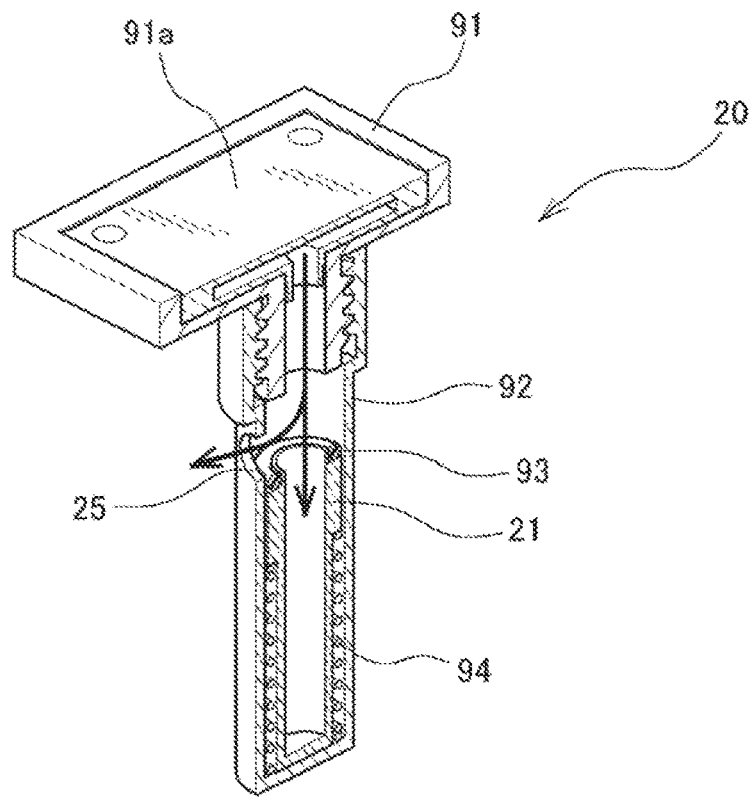
FIG. 9B is a cutaway perspective view depicting the cartridge at the time of emanating a scent pertaining to the third modified example.

The following is a description of the third modified embodiment which is so designed as to control the opening by means of a blower. The third modified embodiment has the cartridge 20 which is constructed as depicted in FIGS. 9A and 9B which are broken perspective views. According to this modified embodiment, the cartridge 20 includes the fragrance holder 21, a blowing unit 91, an outer shell 92, an O-ring 93, and a coil spring 94. The discharge port 25 is provided at the side wall of the outer shell 92. The blowing unit 91 has a built-in blower 91a. The fragrance holder 21 contains the fragrance 22 and the marking material 23, and it also has the O-ring 93 fixed to the top thereof. The coil spring 94 is arranged between the fragrance holder 21 and the outer shell 92 in such a way as to surround the side wall of the fragrance holder 21, and it energizes the fragrance holder 21 upwards.

In the idle state, the fragrance holder 21 is energized upwards by the elastic force of the coil spring 94, so that the O-ring 93 fixed to the top thereof remains in close contact with the lower end of the blowing unit 91. At this time, the discharge port 25 is closed by the side wall of the fragrance holder 21, so that the fragrance holder 21 has its inside kept tightly closed. The cartridge 20 in this state is depicted in FIG. 9A.

When the scent is to be emanated, the blower 91a supplies air stream in response to the control signal from the main body of the scent-emanating apparatus 10. The air supplied in this manner produces a pressure which pushes downwards the fragrance holder 21, so that the discharge port 25 is opened. The air stream produced by the blower 91a generates the gas flow that flows to the outside of the scent-emanating apparatus 10 through the discharge port 25 from the cartridge 20. The gas discharged outwards from the scent-emanating apparatus 10 contains the scent substance and the marker substance. The cartridge 20 in this state is depicted in FIG. 9B. Incidentally, the arrow in the diagram denotes the gas flow.

Unlike the first and second modified embodiments, the third modified embodiment obviates the necessity of providing the power source such as motor and actuator (apart from the blowing mechanism) to open and close the cartridge 20.

Figure 10A:
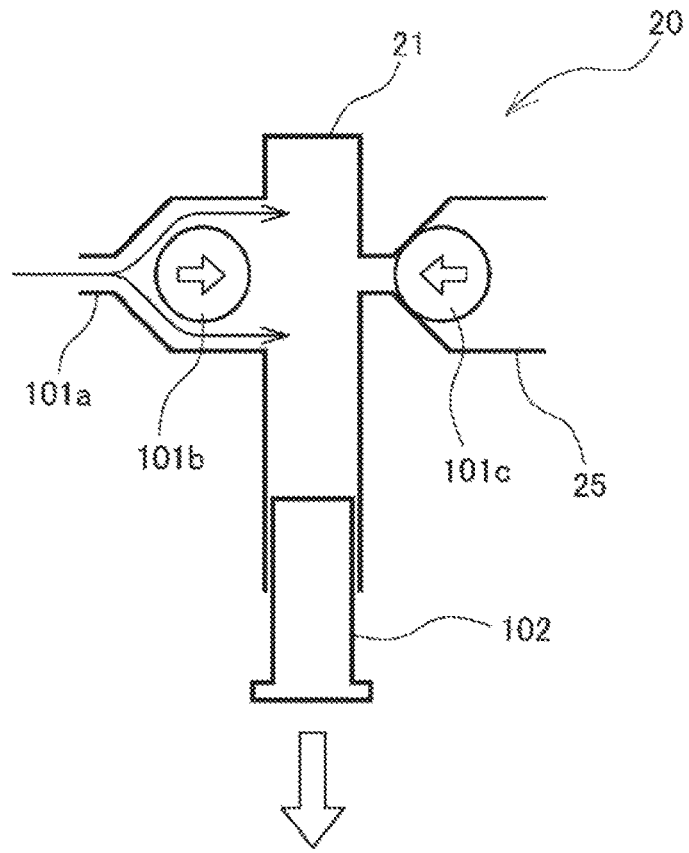
FIG. 10A is a schematic diagram depicting a cartridge in a suction stage pertaining to a fourth modified example.
Figure 10B:
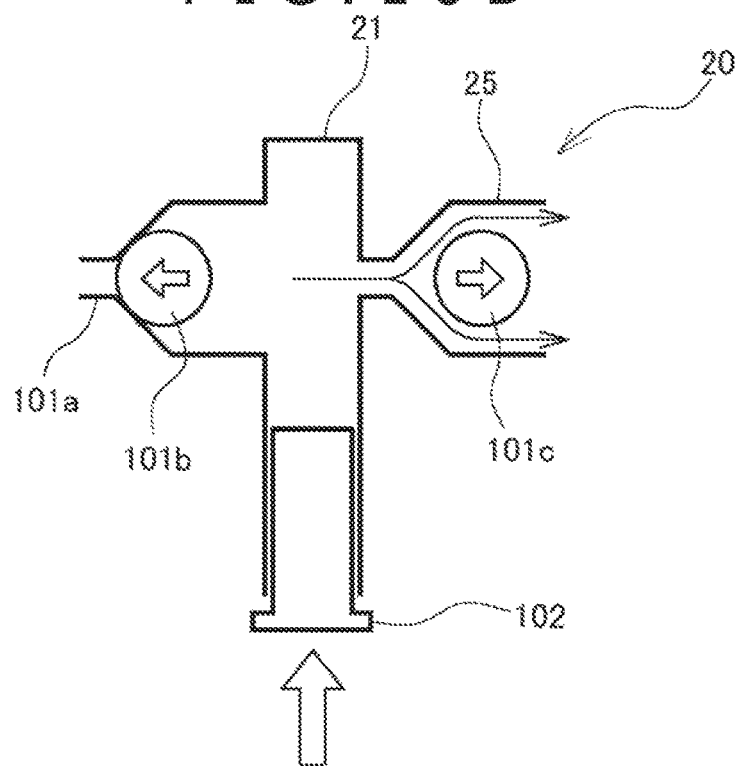
FIG. 10B is a schematic diagram depicting the cartridge in an emission stage pertaining to the fourth modified example.

The following is a description of the fourth modified embodiment which is provided with a diaphragm pump to be actuated by a piston. This modified embodiment has the cartridge 20 which is schematically depicted in FIGS. 10A and 10B. This modified embodiment is designed such that the fragrance holder 21 constitutes the diaphragm pump. The fragrance holder 21 has an inlet 101a and the discharge port 25, with each being provided with check valves 101b and 101c. The check valve 101b blocks the gas flow (through the inlet 101a from the fragrance holder 21) from flowing outwards from the cartridge 20. The check valve 101c blocks the gas flow (through the discharge port 25 from the outside of the cartridge 20) from flowing into the fragrance holder 21. Incidentally, when the cartridge 20 is mounted on the main body of the scent-emanating apparatus 10, a piston 102 is connected to the actuator built in the main body of the scent-emanating apparatus 10.

As the piston 102 is brought down by the actuator, the check valve 101c closes and the check valve 101b opens, so that the gas flows into the fragrance holder 21 through the inlet 101a from the outside of the cartridge 20. This state is depicted in FIG. 10A. After that, the piston 102 is pushed up by the actuator so that the check valve 101b closes and the check valve 101c opens and the gas is discharged to the outside of the cartridge 20 through the discharge port 25 from the fragrance holder 21. This state is depicted in FIG. 10B. Since the fragrance holder 21 contains the fragrance 22 and the marking material 23, the gas discharged from the discharge port 25 contains the scent substance and the marker substance. Incidentally, no matter when the actuator stops, the fragrance holder 21 keeps its internal pressure equal to the atmospheric pressure and the two check valves 101b and 101c remain closed. Consequently, the fragrance holder 21 is kept closed even when the actuator stops unexpectedly.

Figure 11A:
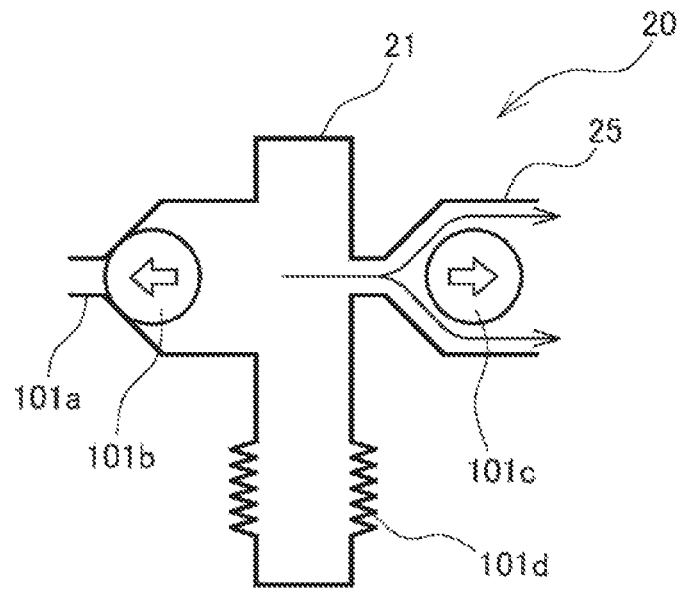
FIG. 11A is a schematic diagram depicting a cartridge in an emission stage pertaining to a fifth modified example.
Figure 11A:
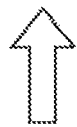
Figure 11B:
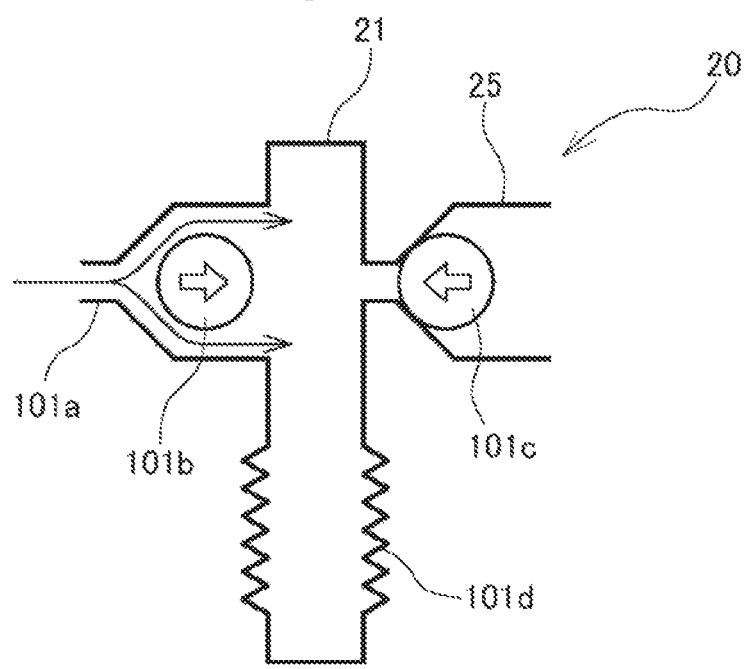
FIG. 11B is a schematic diagram depicting the cartridge in a suction stage pertaining to the fifth modified example.
Figure 11B:
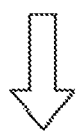

The following is a description of the fifth modified embodiment which employs a diaphragm pump provided with a bellows. The modified embodiment has the cartridge 20 which is constructed as depicted in FIGS. 11A and 11B. As in the case of the fourth modified embodiment, the fifth modified embodiment has the fragrance holder 21 which constitutes the diaphragm pump provided with the inlet 101a and the discharge port 25, having the check valves 101b and 101c, respectively. Also, the fragrance holder 21 is provided with a bellows 101d (having the bellowslike side walls) at the lower part thereof. When the cartridge 20 is mounted on the main body of the scent-emanating apparatus 10, the bellows 101d has its lower end connected to the actuator built in the main body of the scent-emanating apparatus 10.

When the scent is to be emanated, the actuator built in the main body of the scent-emanating apparatus 10 causes the bellows 101d to be pushed upward. This action produces the same effect as that which is produced when the piston 102 is pushed up in the fourth modified embodiment. That is, as the result of this action, the check valve 101c opens, allowing the gas to be discharged to the outside of the cartridge 20 through the discharge port 25 from the fragrance holder 21. This situation is depicted in FIG. 11A. When the actuator pulls the lower end of the bellows 101d, the bellows 101d extends, thereby increasing the volume in the fragrance holder 21. This produces the same effect as in the case where the piston 102 is pulled down in the fourth modified embodiment. That is, as the result of this action, the check valve 101b opens, allowing the gas to be sucked in the fragrance holder 21 from the outside of the cartridge 20 through the inlet 101a. This situation is depicted in FIG. 11B.

The fifth modified embodiment produces the same effect as the fourth modified embodiment. That is, no matter when the actuator may be suspended, the two check valves 101b and 101c are closed, so that the fragrance holder 21 is kept completely sealed. In addition, the fifth modified embodiment is advantageous over the fourth modified embodiment in that the fragrance holder 21 is sealed more air tight than in the fourth modified embodiment which employs the piston 102 because the bellows 101d is kept sealed from the beginning. Another advantage of the fourth and fifth modified embodiments is that they do not need the power source (apart from that for blowing) to open and close the valves as in the case of the third modified embodiment.

Incidentally, each of the modified embodiments mentioned above may have the deodorizing mechanism attached to the cartridge 20 or have the gas sensor 26 mounted on each of the cartridges 20 or on the main body of the scent-emanating apparatus 10. The foregoing description merely exemplifies the structure and configuration of the scent-emanating apparatus 10 according to the embodiments and modified embodiments. The scent-emanating apparatus 10 according to the embodiment of the present invention will be variously modified in structure and shape so as to realize the functions mentioned above.

REFERENCE SIGNS LIST

1 Scent-emanating system
10 Scent-emanating apparatus
11 Control circuit
12 Interface
13 Cartridge holder
20 Cartridge
21 Fragrance holder
22 Fragrance
23 Marking material
24 Discharging mechanism
25 Discharge port 25a Discharge valve
26 Gas sensor
27 Deodorant
28 Deodorizing filter
29 Memory
30 Information processing apparatus
31 Control unit
32 Memory unit
33 Interface unit
40 Operating device
50 Display apparatus

The invention claimed is:

1. A scent-emanating product to emanate a scent substance to a user, comprising:
   a cartridge holder;
   a fragrance holder contained in the cartridge holder, wherein the fragrance holder is removable from the cartridge holder;
      wherein the fragrance holder comprises:
         an inlet port;
         an outlet port,
         wherein the inlet port and the outlet port are sealed when the fragrance holder is not in use;
         a marker container for holding a marker substance; and
         a fragrance container for holding a fragrance substance,
         wherein the marker container holds the marker substance separately from the fragrance substance in the fragrance container;
   a single outlet port coupled to the outlet port for discharging the fragrance substance and the marker substance simultaneously,
   a discharging mechanism coupled to the inlet port for causing the fragrance substance and the marker substance to be discharged through the single outlet port outwards from the scent-emanating product; and
   a sensor to only detect the marker substance discharged from the single outlet port and not the fragrance substance,
   wherein the marker substance does not have a scent that can be sensed by the user at all and does not cancel the scent of the scent substance; and
   wherein the discharging mechanism outputs the fragrance substance until the sensor detects a marker substance concentration in a range of a predetermined value.

2. The scent-emanating product according to claim 1, further comprising:
   a deodorant holder for holding a deodorant substance separate from the cartridge holder,
   wherein the discharging mechanism reverses airflow which causes the inlet and the outlet port to seal and for air to pass over the deodorant substance in the deodorant holder.

3. The scent-emanating product according to claim 1, wherein the marker substance is alcohol or carbon dioxide.

* * * * *